June 8, 1965 J. G. DU PUIS, JR Plant Pat. 2,529
AVOCADO TREE
Filed April 13, 1964
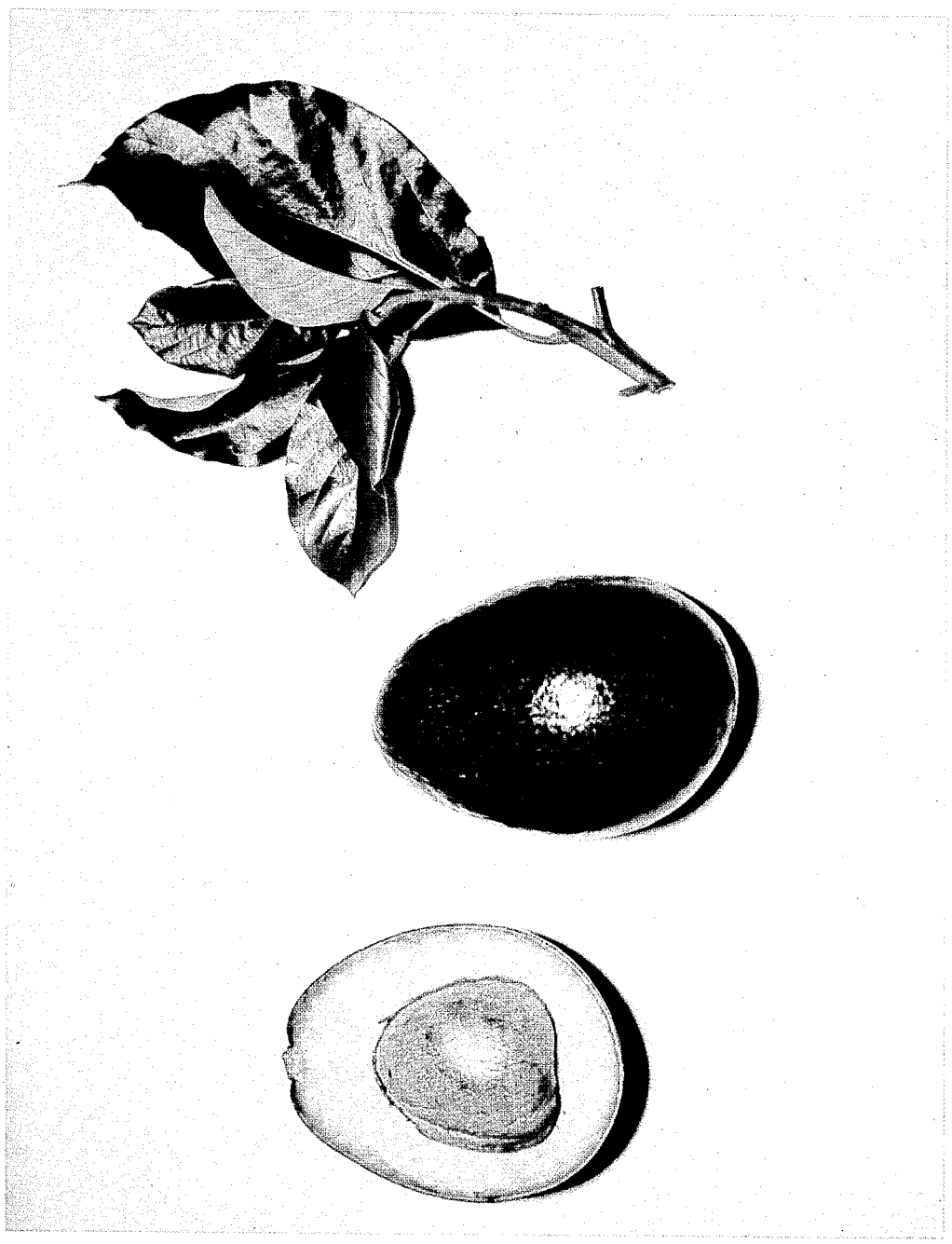
John G. DuPuis Jr United States Patent Office Plant Pat. 2,529
Patented June 8, 1965

2,529
AVOCADO TREE

John G. Du Puis, Jr., 6000 NW. 32nd Ave., Miami, Fla.
Filed Apr. 13, 1964, Ser. No. 359,535
1 Claim. (Cl. Pit.—44)

This invention pertains to a new and distinct variety of avocado tree which has certain highly desirable characteristics. During the early part of the avocado season in Florida, namely June and July, the market desires an attractive medium-sized avocado fruit with a comparatively small seed tight in its cavity, with a firm, yellow, high quality flesh, and with the capability of being shipped some distance to market.

From the viewpoint of the grower, trees should be not too spreading and should be relatively upright in growth to alleviate crowding in the grove and allow for adequate cultivation. It should be a vigorous growing type and quite resistant to the more common diseases, such as avocado scab. Blooming should be early to help insure earlier maturity and the trees should have the inherent ability to set heavy, but well distributed, crops of fruit each year.

The tree of this new variety answers all of the general specifications listed above, plus others. The tree exhibits exceptional vigor; buds and grafts of this tree on other root-stocks produced young plants with outstanding vigor. Several larger trees topworked with graftwood from this tree also exhibit excellent vigor and have produced good crops of uniform fruit each year.

This new variety originated as a limb mutation in my grove at Miami, Florida, from a hybrid seedling of unknown parentage, probably of West Indian origin. The quality of the fruit of this mutation was far superior to the original tree, so therefore was selected to be reproduced asexually by budding and grafting, by me, in my grove in Miami. There was no apparent variation from the original mutation through these experiments.

Accompanying illustrations show, in approximately true color, a specimen of the fruit, a cross-section of another specimen, and a small twig with both juvenile and mature leaves.

The new varity of avocado tree to which this invention is directed is a tree of moderately upright, compact growth; symmetrical with evenly distributed branches.

The leaves are obovate, opening flat, alternately spaced on twigs and branches. All green wood has plump buds at the leaf axils. The leaf tip is sub-acute; the base of the leaf is cuneate. The margins of the leaf are entire with an occasional slight undulation. On the upper surface of the leaves, the main veins are lighter colored green than lamina and quite distinct.

Juvenile leaves are bronze-like in color (Dictionary of Color, Maerz and Paul, Plate 15, A–C–E, 10–11–12) with distinct veining in the range of Sea Green (Plate 19, J–K–L, 4–5–6). Underside of the leaves has a similar color but in a duller shade.

The large mature leaves are slightly glossy on the upper surface of a dark green color (Plate 23, J–L, 8–9–10). Undersides are a dull lighter green (Plate 20, C–D, 5–6). The stems are darker than Shadow Green (Plate 20, I–J, 4–5–6) with occasional lenticels.

Blooming takes place in February, with the flowers appearing both as terminal and axillary clusters. The flowers are perfect and have the characteristics dichogamy of other forms of *Persea americana*.

The variety has the ability to set and hold a well distributed crop of young fruits under adverse weather conditions, making it more desirable as a commercial crop. The fruit matures from mid June to early August.

The fruit is broadly oval to pyriform, slightly flattened on one side toward the apex. The rich green skin (Plate 19, J–K–L, 7–8–9) is slightly rough with frequent occurrence of conspicuous cream-colored stomato over all. The skin is rather thick for a summer-fruiting avocado. The heavy, strong stem-button is set in a slight depression and the rather short stem, 1 to 2 inches long, is firmly attached to both the fruits and the branchlet. Fruit vary in weight from 12 to 20 ounces, mostly averaging 15 to 16 ounces. Length is from 5 to 6 inches and width from 3½ to 4 inches.

The medium-sized to large seed fits tightly in its cavity and has a closely adhering, light brown covering. It is almost round in shape and comes to a very small point at the proximal end.

The flesh of the fruit is firm, free of fiber and has a very rich, almost almond-like flavor. The deep yellow coloring (Plate 18, J–K–L, 1) blends into the light green (Plate 18, K–L, 6–7–8) cortex, just beneath the skin.

The distinguishing characteristics of the tree of this invention are the distinctive appearance of the fruit with its high market quality, the ability to set and hold fruit during adverse weather conditions, symmetrical, semi-upright growth allowing for easy grove culture, its resistance to avocado scab as brought out by observations and tests in both grove and nursery, and its early season maturity. It is readily understood that perhaps during different seasons or in different localities the growth habits might vary within the range of common error but the description as given is true. This tree can be recommended for planting in the lower east coast region of Florida as well as the off-shore islands to the east and south.

Having thus disclosed my invention, I claim:

The new and distinct variety of avocado tree, substantially as herein shown and described, characterized particularly by its moderately upright, compact growth, with evenly distributed branches; a flowering period occurring early in February, fruit maturing season each year from mid June to early August; and the ability to set and hold fruit under adverse weather conditions; the fruit being further characterized as broadly oval, having slightly rough, thick skin with conspicuous cream-colored stomata over all; seed that is in good proportion to the flesh and the flesh is firm, free of fiber, and of a delicate nutty flavor.

No references cited.

ABRAHAM G. STONE, *Primary Examiner.*